United States Patent [19]
Vanlerberghe et al.

[11] 3,940,477
[45] Feb. 24, 1976

[54] COSMETIC SKIN COLORING COMPOSITIONS CONTAINING AMINATED γ-DIALDEHYDES

[75] Inventors: Guy Vanlerberghe, Par Claye-Souilly; Georges Rosenbaum, Asnieres, both of France

[73] Assignee: L'Oreal, Paris, France

[22] Filed: May 8, 1974

[21] Appl. No.: 468,086

Related U.S. Application Data

[63] Continuation-in-part of Ser. No. 210,217, Dec. 20, 1971, Pat. No. 3,812,246.

[30] Foreign Application Priority Data
Dec. 24, 1970 Luxemburg............................. 62317

[52] U.S. Cl................................. 424/59; 424/63
[51] Int. Cl.² ..................... A61K 7/021; A61K 7/42
[58] Field of Search................................. 424/59, 63

[56] References Cited
UNITED STATES PATENTS

| | | | |
|---|---|---|---|
| 3,781,418 | 12/1973 | Pomot et al. | 423/63 |
| 3,812,246 | 5/1974 | Vanlerberghe et al. | 424/63 |

*Primary Examiner*—Donald B. Moyer
*Attorney, Agent, or Firm*—Cushman, Darby & Cushman

[57] ABSTRACT

Aminated aldehydes are usefully employed in cosmetic compositions to tan the skin.

8 Claims, No Drawings

COSMETIC SKIN COLORING COMPOSITIONS CONTAINING AMINATED Γ-DIALDEHYDES

This application is a continuation-in-part of our application Ser. No. 210,217, filed Dec. 20, 1971 now U.S. Pat. No. 3,812,246.

The present invention relates to an animated aldehyde having the formula

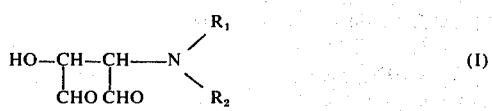

wherein $R_1$ is selected from the group consisting of hydrogen, alkyl, hydroxyalkyl, cycloalkyl, aryl, alkaryl, (2,5-dialkoxy-4-hydroxy)-3-tetrahydrofuryl wherein each of the alkoxy moieties has 1–4 carbon atoms, β-N-[(2,5-dialkoxy-4-hydroxy)-3-tetrahydrofuryl]-aminoethyl wherein each of the alkoxy moieties has 1–4 carbon atoms, $R_2$ is selected from the group consisting of hydrogen, alkyl, hydroxyalkyl, cycloalkyl, aryl, alkaryl, (1,2-diformyl-2-hydroxy) ethyl, 2-[(1,2-diformyl-2-hydroxy) ethyl amino] ethyl, and $R_1$ and $R_2$ together with the nitrogen atom to which they are attached form a heterocycle selected from the group consisting of piperdinyl and morpholinyl. Representative alkyl substituents are those having 1–6 carbon atoms while useful hydroxalkyl substituents are those wherein the alkyl moiety has 1–6 carbon atoms such as hydroxyethyl. Representative cycloalkyl substituents include those having 3–6 carbon atoms and especially cyclohexyl, whereas useful aryl substituents include phenyl, naphthyl and the like. The alkyl moiety of the alkaryl substituent can have, preferably, from 1–6 carbon atoms while the aryl moiety can be, for instance, phenyl, naphthyl or the like. A preferred alkaryl substituent is benzyl.

The present invention also relates to the quaternary ammonium salts of the aminated aldehydes of formula (I), said quaternary ammonium salts having the formula

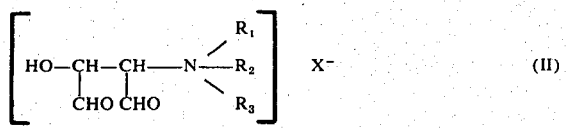

wherein $R_1$ is selected from the group consisting of alkyl, hydroxyalkyl, cycloalkyl, aryl, alkaryl, (2,5-dialkoxy-4-hydroxy)-3-tetrahydrofuryl wherein each of the alkoxy moieties has 1–4 carbon atoms, β-N-[(2,5-dialkoxy-4-hydroxy)-3-tetrahydrofuryl]-aminoethyl wherein each of the alkoxy moieties has 1–4 carbon atoms, $R_2$ is selected from the group consisting of hydrogen, alkyl, hydroxyalkyl, cycloalkyl, aryl, alkaryl, (1,2-diformyl-2-hydroxy) ethyl, 2-[(1,2-diformyl-2-hydroxy) ethyl amino] ethyl, and $R_1$ and $R_2$ together with the nitrogen atom to which they are attached form a heterocycle selected from the group consisting of piperidinyl and morpholinyl. Representative alkyl substituents are those having 1–6 carbon atoms and, advantageously, methyl or ethyl. Useful hydroxyalkyl substituents are those wherein the alkyl moiety has 1–6 carbon atoms, such as hydroxyethyl. Representative cycloalkyl substituents include those having 3–6 carbon atoms and, especially, cyclohexyl. The alkyl moiety of the alkaryl substituent can have, preferably, from 1–6 carbon atoms while the aryl moiety again can be phenyl, naphthyl or the like. A preferred alkaryl substituent is benzyl. $R_3$ represents a member selected from the group consisting of lower alkyl having 1–6 carbon atoms and benzyl, substituted or not and $X^-$ represents a member selected from the group consisting of chloride, bromide, iodide, methosulfate, ethosulfate, paratoluene sulfonate and methane sulfonate. A preferred value for $R_3$ is methyl while preferred values for $X^-$ are chloride, methosulfate, paratoluene sulfonate and methane sulfonate.

The above aminated aldehydes of formulae (I) and (II) correspond to 2-amino-3-hydroxy aldehyde and to the N-substituted derivatives thereof.

The present invention also relates to the preparation of the aminated aldehydes having formula (I) and of the quaternary ammonium salts thereof having the formula (II).

Further, the present invention also relates to a cosmetic composition containing at least one aminated aldehyde having formula (I) and/or at least one quaternary ammonium salt thereof having formula (II).

The aminated aldehydes of formula (I) can be prepared by acid hydrolysis of a 2,5-dialkoxy 3-amino 4-hydroxytetrahydrofuran and the N-substituted derivatives thereof having the formula

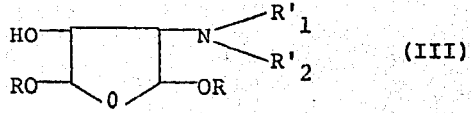

wherein $R'_1$ and $R'_2$ each independently are selected from the group consisting of hydrogen, alkyl, hydroxyalkyl, cycloalkyl, aryl, alkaryl, (2,5-dialkoxy-4-hydroxy)-3-tetrahydrofuryl wherein each of the alkoxy moieties has 1–4 carbon atoms, β-N-[(2,5-dialkoxy-4-hydroxy)-3-tetrahydrofuryl]-aminoethyl wherein each of the alkoxy moieties has 1–4 carbon atoms, and together with the nitrogen atom to which they are attached form a heterocycle selected from the group consisting of piperdinyl and morpholinyl. Representative alkyl substituents are those having 1–6 carbon atoms while useful hydroxyalkyl substituents are those wherein the alkyl moiety has 1–6 carbon atoms such as hydroxyethyl. Representative cycloalkyl substituents include those having 3–6 carbon atoms and especially cyclohexyl, whereas useful aryl substituents include phenyl, naphthyl and the like. The alkyl moiety of the alkaryl substituent can have, preferably, from 1–6 carbon atoms while the aryl moiety can be, for instance, phenyl, naphthyl or the like. A preferred alkaryl substituent is benzyl.

The quaternary ammonium salts of aminated aldehydes having formula (II) can be prepared by acid hydrolysis of the quaternary ammonium salts of N-disubstituted 2,5-dialkoxy 3-amino 4-hydroxy tetrahydrofurans having the following formula:

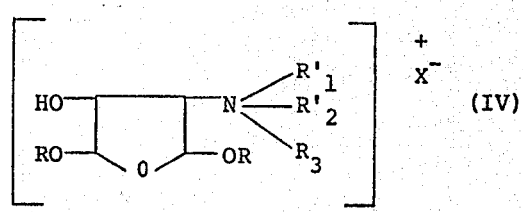

wherein $R'_1$, $R'_2$, $R_3$ and $X^-$ have the meanings indicated above and R represents alkyl having 1–4 carbon atoms, preferably methyl.

In the acid hydrolysis reaction medium the concentration of the compound having formula (III) or (IV) to be hydrolyzed can vary within wide limits and, preferably, a concentration of 0.01 to 1 mole/liter is employed.

There is heated, for example, in a boiling water bath, an acid solution of the compound having formula (III) or (IV) for a time that can range from about 5 minutes to several hours. The acid medium is obtained by addition of a strong mineral or organic acid, such as HCl, $H_2SO_4$, paratoluene sulfonic acid or methane sulfonic acid up to a concentration of about 0.1 to 5 N. The reaction mass is generally heated to a temperature of about 20° to 100°C.

The aminated aldehydes of formulae (I) and (II) can also be prepared by acid hydrolysis of their corresponding tetraalkyl acetals having formulae (V) and (VI), respectively:

It is to be noted that the 2,5-dialkoxy tetrahydrofurans and their derivatives represented by formulae III and IV present cis-trans isomerism at the level of the alkoxy groups in positions 2 and 5. The substituents in positions 3 and 4 can likewise increase the number of possible isomers. The isomers often are detectable by gas chromatography and sometimes they can be isolated by fractional distillation.

Certain of the 2,5-dialkoxy tetrahydrofurans of formula (III) are new compounds. They are those wherein R represents alkyl having 1 to 4 carbon atoms, preferably the methyl radical; and wherein $R'_1$ represents hydroxyalkyl, cycloalkyl, aryl, alkaryl radical having up to 12 carbon atoms, (2,5-dialkoxy 4-hydroxy)-3-tetrahydrofuryl and β-N-[(2,5-dialkoxy 4-hydroxy)-3-tetrahydrofuryl]-aminoethyl and wherein $R'_2$ represents hydrogen or the immediately above meanings indicated for $R'_1$. In these new tetrahydrofurans, the alkyl moiety in hydroxyalkyl and alkaryl radicals preferably is cyclohexyl, while the preferred aryl substituent is phenyl, the

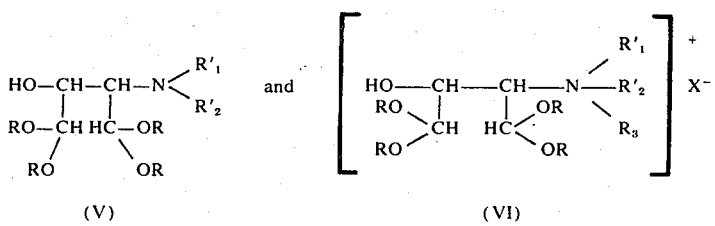

(V) and (VI)

In formula (V), $R'_1$ and $R'_2$ have the meanings indicated above and R represents an alkyl having 1–4 carbon atoms, preferably methyl. In formula (VI) $R'_1$, $R'_2$, $R_3$ and $X^-$ have the meanings indicated above and R represents an alkyl having 1–4 carbon atoms, preferably methyl.

Once the hydrolysis reaction has been terminated, these solutions respectively, contain aminated aldehydes of formula (I) or quaternary ammonium salts of formula (II) depending on whether the starting compound was of formula (III) or (V), or a compound of the formula (IV) or (VI).

The solutions which result from the hydrolysis reaction yield characteristic reactions of aldehydes, such as reduction of hypoiodite, formation of oximes and dinitrophenylhydrazones.

The aldehydes in the hydrolyzed solutions are characterized either by their reaction with dinitrophenylhydrazine to produce a dinitrophenylhydrazone or by hypoiodite determination.

In the first case there is employed an excess of solution of 0.2% 2,4-dinitrophenylhydrazine in 2N HCl, and after a period of standing the dinitrophenylhydrazones that are formed are separated by filtration. They are then washed with 2N HCl, dried and analyzed.

In the second case the procedure followed is that embodied in the method adopted by Robinson and McLeod, which is described in Loiseleur's book, "Laboratory Technique", page 1344 (Masson Edition).

The aminated aldehydes of formula (I) area only stable in strongly acid solution, with the primary amino compounds being less stable than the secondary and tertiary compounds.

preferred hydroxyalkyl substituent is hydroxyethyl and the preferred alkaryl substituent is benzyl.

2,5-dialkoxy 3-amino 4-hydroxy tetrahydrofurans especially 2,5-dimethoxy 3-amino 4-hydroxy tetrahydrofurans, and the N-substituted derivatives thereof having formula (III), quaternary ammonium salts having formula (IV), tetraalkyl acetals having formula (V) and quaternary ammonium salts of tetraalkyl acetals having formula (VI) are valuable intermediate products which by way of acid hydrolysis provide useful solutions for the preparation of cosmetic compositions, particularly for the coloring of the skin and the strengthening of the restructuring of the hair.

The salts of the 2,5-dialkoxy 3-ammonio 4-hydroxy tetrahydrofurans of formula (IV) are also new compounds.

Moreover, the aminated aldehydes of formula (I) and their quaternary ammonium salts having formula (II) are also new compounds.

The 2,5-dialkoxy tetrahydrofurans and their N-substituted derivatives of formula (III) can be prepared according to the following methods A and B.

Method A

Reaction of an amine having the formula

wherein $R'_1$ and $R'_2$ have the meanings indicated for the compound of formula (III) on a 2,5-dialkoxy-3, 4-epoxytetrahydrofuran having formula (VIII) wherein R represents alkyl having 1 to 4 carbon atoms.

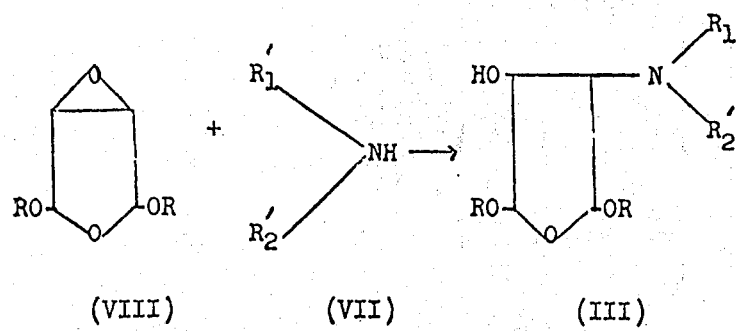

(VIII)    (VII)    (III)

The 2,5-dialkoxy-3,4-epoxy tetrahydrofuran of formula (VIII) can, in turn, be prepared from 2,5-dialkoxy-3-halogene-4-hydroxytetrahydrofuran having formula (IX) below, in which Hal designates chlorine or bromine and R has the meaning indicated above.

In practice, to effect reaction A, a procedure in accordance with (a) or (b) is followed:

a. Use of the Amine in Stoichiometric Quantity

There is heated at a temperature between 50° and 100°C for example, in a boiling water bath for several hours, preferably between 20 and 110 hours, a mixture which contains a 2,5-dialkoxy-3,4-epoxy tetrahydrofuran and a stoichiometric quantity of the amine, either without solvent or in aqueous or aqueous alcoholic solution. At the end of the heating period the solvent is evaporated off if required, and the compound of formula (III) is isolated by distillation, crystallization or any other appropriate method. The aqueous alcohol solution can comprise between about 10 to 90 percent of an alcohol such as methanol, ethanol or isopropanol.

b. Use of Excess Amine

In this alternative procedure, after the end of the heating period the remaining amount of amine is driven off under reduced pressure, as well as the solvent if necessary, and the product is isolated as indicated above. Generally, the molar ratio of amine to epoxy tetrahydrofuran will range from about 50:1 to 1.5:1.

Method B

Reaction of an excess of the amine having formula VII wherein $R'_1$ and $R'_2$ have the meaning indicated above, preferably, in the presence of an alkali metal hydroxide, such as sodium or potassium hydroxide with a compound having formula (IX), according to the following scheme:

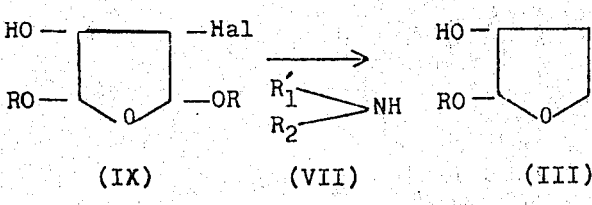

(IX)    (VII)    (III)

The alkali metal hydroxide can be used in stoichiometric or in slight excess with respect to compound (IX).

To effect reaction B, a procedure in accordance with (c) or (d) is followed.

c. Introduction of Alkaline Metal Hydroxide After Heating

There is heated in a boiling water bath, for example, for several hours, preferably between 20 and 110 hours, a reaction mixture which contains a 2,5-dialkoxy-3-halogeno-4-hydroxytetrahydrofuran [compound of formula (IX)] and an excess of the amine having formula (VII). The molar ratio amine: tetrahydrofuran ranges from 50:1 to 2:1 and preferably, there are used 5 moles or more amine per mole of compound of formula (IX). An aqueous or an aqueous alcoholic solution as defined above can be employed. The concentration of the amine solution is not of primary importance, but it is preferable to use a solution wherein the amine concentration ranges between about 5 to 10 moles/liter.

After the end of the heating period there is added in the form of a 10 N solution, an alkali metal hydroxide, such as sodium or potassium hydroxide, in equimolar quantity with reference to the compound of formula (IX) which was originally introduced. This is followed by evaporation to dryness under reduced pressure. The residue is taken up in alcohol such as ethyl alcohol and the mineral salts are eliminated by filtration. There is a repeated evaporation to dryness under reduced pressure. The compound of formula (II) is separated from the residue by distillation, crystallization or by any other suitable separation technique.

d. Introduction of the Alkaline Metal Hydroxide before Heating

As a variant of procedure (c), sodium hydroxide or potassium hydroxide is introduced at the start, before heating is commenced. The remaining procedure is that described above for procedure (c).

The present invention also relates to a process for the preparation of the quaternary ammonium salts of formula (IV) by reaction of a quaternizing agent $R_3X$ on a compound having formula (III). As quaternizing agent there can be used lower $C_1$–$C_4$ halides, substituted or unsubstituted benzyl halides, lower dialkyl sulfates, lower alkyl tosylates and lower alkyl mesylates, said lower alkyls having 1 to 4 carbon atoms. This reaction is effected according to the following scheme:

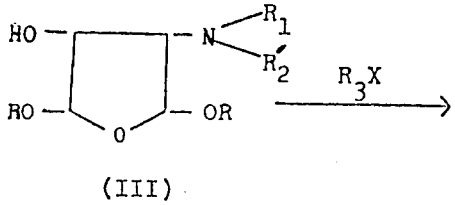

(III)

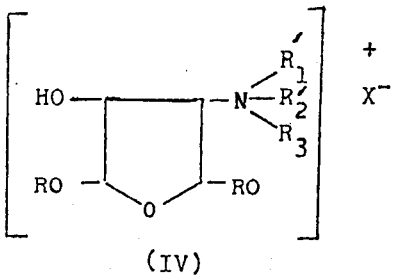

(IV)

There is added, for example, drop by drop, to a compound of formula (III) in ether solution, with cooling, a stoichiometric quantity of the quaternizing agent. The quaternary ammonium salt separates out. The mixture is allowed to stand, the solvent is decanted, the residue is washed with ether, and thereafter is dried under vacuum.

The present invention further relates to the use of (1) aminated aldehydes of formula (I), (2) the quaternary ammonium salts of formula (II), (3) the acid hydrolysis product of a 2,5-dialkoxy-3-amino-4-hydroxy tetrahydrofuran or its N-substituted derivative of formula (III), (4) the acid hydrolysis product of a quaternary ammonium salt having formula (IV), (5) the acid hydrolysis product of a tetraalkyl acetal having formula (V), and (6) the acid hydrolysis product of the quaternary ammonium salt of a tetraalkyl acetal having formula (VI), for the coloring of the skin and the strengthening or the restructuring of the hair.

It has been found that the aminated aldehydes of the present invention impart to the skin a color which is similar to that which it acquires by more or less lengthy exposure to the sun or to ultraviolet rays. The ability of the aldehydes of the present invention to color the skin varies according to the degree of substitution of the amino group and according to the nature of the substituents.

It has also been observed that the most active compounds are the secondary amines and next the primary amines and then the tertiary amines. Quaternary compounds do not color the skin but are usefully employed to strengthen or restructure the hair.

The present invention also relates to a cosmetic composition for coloring the skin, comprising a solution of at least one aminated aldehyde as defined above, the nitrogen atom of which is unsubstituted, mono-substituted or disubstituted.

The pH of this composition can vary between 2–7 and preferably between 2–5.

The cosmetic composition of this invention for coloring the skin can be provided under the following forms:
1. an aqueous solution or a hydroalcoholic solution wherein the alcohol can be ethanol or isopropanol;
2. a glycerine-hydroethanol or glycerine-hydroisopropanol solution;
3. an oleo-ethanol composition;
4. an aqueous gel including a surface active agent, a gel former and optionally a silicone oil, and
5. an oil-in-water emulsion.

The aqueous solution, hydroalcoholic solution, glycerine-hydroethanol solution and glycerine-hydroisopropanol solution can also include perfume, as well as other conventional adjuvants. The glycerine is present in an amount between about 0.5–5% and preferably about 2% by weight of the composition. Ethanol and isopropanol are present in an amount of about 10–90 percent by weight of the total composition.

The oleo-ethanolic composition contains:

i. 0.2–5% of a vegetable oil, for example colza oil, olive oil, peanut oil, cocoa oil and palm oil;
ii. 5–40% of a lower alkyl ester selected from the group consisting of isopropyl myristate and isopropyl palmitate; and
iii. 35–80%, preferably 40–75% of ethanol.

The oleo-ethanolic composition can be packaged under pressure in an aerosol container with a propellant selected from the group consisting of dichlorodifluoromethane, trichloromonofluoromethane and their mixtures, as well as other conventional propellants. The oleo-alcoholic composition can also include perfume as well as other conventional cosmetic adjuvants.

The aqueous gel composition contains;
i. a surface active agent;
ii. a gel former, i.e. thickening agent,
iii. optionally silicone oil;
iv. the aminated aldehyde defined above; and
v. the remainder essentially water.

Generally there is employed between 1–15% and preferably 1–13% of the surface active agent selected from the group consisting of A. fatty alcohols having 12–18 carbon atoms and oxyethylenated with 4–15 and preferably 6–12 mols of ethylene oxide;

B. nonylphenol oxyethylenated with 6–12 mols of ethylene oxide; and

C. a carboxylic derivative of imidazole sold under the name "MIRANOL" and preferably "MIRANOL C2M" of the formula

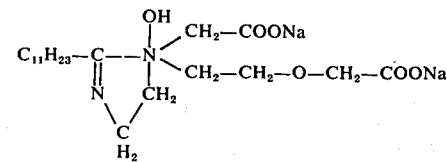

Also there is usually employed about 0.5–4% and preferably 1–2.5% of the gel former or thickening agent selected from the group consisting of A. cellulose ethers, for example, the methyl, ethyl and isopropyl ethers of cellulose;

B. carboxymethyl cellulose; and

C. crosslinked polyacrylic acids sold under the name "CARBOPOL".

The most useful CARBOPOLS are CARBOPOL 934, CARBOPOL 940 and CARBOPOL 941. Their Brookfield viscosities, measured in a 0.5% solution neutralized to a pH 7 with NaOH are as follows:

| | |
|---|---|
| CARBOPOL 934 | 32,500 centipoises |
| CARBOPOL 940 | 43,000 centipoises |
| CARBOPOL 941 | 8,900 centipoises |

Generally when there is employed as the surface active agent the carboxylic derivatives of imidazole sold under the mark "MIRANOL", it is preferable to use as the gel former the crosslinked polyacrylic acids sold under the mark "CARBOPOL".

The aqueous gels of this invention can also include 0–2% and preferably 0–1% of silicone oil. The silicone oil when it is present is found to be emulsified by the surface active agent.

The oil-in-water emulsions of this invention contain:
i. 2–15% of a surface active agent selected from the group consisting of
A. an emulsifier selected from the group consisting of fatty alcohols having 12–18 carbon atoms and oxyethylenated with 10–15 moles of ethylene oxide,
B. a self-emulsifiable wax selected from cetylstearyl alcohols, partially sulfated or partially oxyethylenated; and
C. mixtures of (A) and (B);
ii. 0–20% as the fatty or "oil" phase a component selected from the group consisting of light vaseline oil, perhydrosqualene, vegetable oil, for example sweet almond oil, ricin oil, colza oil, olive oil, peanut oil, cocoa oil or palm oil, a fatty alcohol having 16 carbon atoms and a saturated fatty acid having 18 carbon atoms, isopropyl palmitate and isopropyl myristate;
iii. 0–6% of a thickening agent selected from the group consisting of
A. starch,
B. crosslinked polyacrylic acids sold under the mark "CARBOPOL", and
C. diethylene glycol stearate;
iv. 0–15% glycerine and
v. the remainder essentially water.

When the surface active agent is cetyl stearyl alcohol partially oxyethylenated, or partially sulfated, the non-oxyethylenated or non-sulfated part of the fatty alcohol serves as the fatty or "oil" phase in the oil-in-water emulsion. The glycerine serves to soften the skin and improve the wetting characteristics of the composition.

The oil-in-water emulsions can be provided in the form of a milk or a cream. They can also be packaged under pressure in an aerosol container with a propellant selected from the group consisting of dichlorodifluoromethane and trichloromonofluoromethane as well as mixtures thereof or other propellants conventionally used in aerosol type cosmetic formulations.

The active component, aminated aldehyde, is generally present in amounts of 0.5–12% by weight of the total composition for the coloration of the skin.

The aminated aldehydes of the present invention effect a strengthening, restructuring or regeneration of the hair, with an improvement of its cosmetic quality.

This regeneration or restructuring generally is effected on bleached hair or on hair that has undergone a treatment for permanents. It also can be used on hair which has undergone a reduction that constitutes the first stage of a "permanent wave" operation and before the second stage thereof, that is to say, the neutralizing operation.

This restructuring or strengthening of the hair is evidenced by a better appearance and an improved feel, softness and liveliness of the hair and general improvement of its cosmetic quality.

Usually this treatment to strengthen or restructure the hair is effected by applying to the hair a cosmetic composition containing at least one aminated aldehyde of formula (I) and/or a quaternary ammonium salt of formula (II), the pH of the solution being between 1.5 and 9, preferably between 2 and 5 and permitting said composition to remain in contact with the hair for a period of about 5–60 minutes at a temperature generally between about 15° and 50° C. The hair is then rinsed and if desired rolled on curlers and dried.

Thus the present invention also relates to a cosmetic composition for strengthening or restructuring the hair, said composition comprising an aqueous or aqueous alcoholic solution of about 20 to 70 weight percent of an alkanol such as ethanol or isopropanol of at least one aminated aldehyde of formula (I) and/or a quaternary ammonium salt of formula (II), the pH of the solution being between 1.5 and 9, preferably between 2 and 5. The aminated aldehyde or its quaternary ammonium salt is generally present in amounts of about 2 to 25 and preferably 3 to 18 percent by weight of said composition.

Such a composition can include other cosmetic ingredients and be in the form of a solution, a cream or a gel. It also can be stored under pressure in aerosol containers together with an aerosol propellant such as dichlorodifluoromethane, trichloromonofluoromethane, their mixtures as well as other conventional aerosol propellants.

Unless otherwise stated, all parts and percentages are by weight.

In order to better illustrate the invention, the following examples of the preparation of the compounds of this invention and their use are given below.

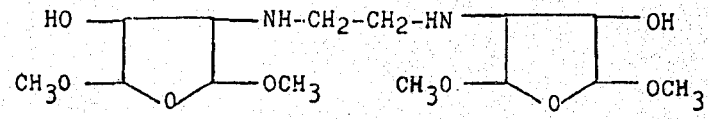

EXAMPLES OF PREPARATION

Preparation of compounds of formula (III)

Example 1 — Method A — procedure (a), preparation of 3,3'-ethylene diamimo-bis-(2,5-dimethoxy-4-hydroxytetrahydrofuran) having formula:

There is heated in a boiling water bath for 108 hours a mixture of:
29.2 g of 2,5-dimethoxy-3,4-epoxy tetrahydrofuran
6.08 g of 98.5% ethylene diamine and
3.5 ml of water The development of the reaction is followed by gas chromatography. After the conclusion of the heating period the water is driven off under reduced pressure, and reagents that have not reacted are eliminated by distillation under 0.1 mm Hg, heating by means of an oil bath at 200°C. As distillation residue there is obtained 31.65 g of the compound indicated above, in the form of a syrupy red liquid.

Example 2 — Method A — procedure (b), preparation of 2,5-dimethoxy-3-piperidino-4-hydroxytetrahydrofuran having the formula:

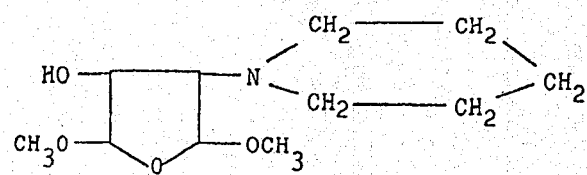

There is heated in a boiling water bath for 48 hours, a mixture of:
14.6 g of 2,5-dimethoxy-3,4-epoxy tetrahydrofuran
55 ml of piperidine
7 ml of water After the conclusion of the heating period the water and excess piperidine are driven off under reduced pressure and the product is distilled. 19.3 g of the compound indicated above are obtained. Example 3 — Method B — procedure (c), preparation of 2,5-dimethoxy-3-amino-4-hydroxy tetrahydrofuran having the formula:

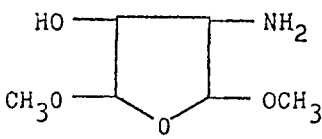

There is heated in a boiling water bath for 20 hours a mixture of 27.4 g of 2,5-dimethoxy-3-chloro-4-hydroxytetrahydrofuran and 300 ml of concentrated NH$_4$OH (22° Be). During this heating period there are added in five operations at regular time intervals 150 ml of NH$_4$OH. After conclusion of the heating period there are added 15 ml 10 N NaOH, with evaporation to dryness under reduced pressure. The residue is taken up in ethyl alcohol, filtered and distilled under vacuum. There are obtained 19.25 g of the compound indicated above.

Example 4 — Method B — procedure (d), preparation of 2,5-dimethoxy-3-ethylamino-4-hydroxytetrahydrofuran having the formula:

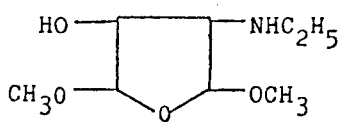

There is heated in a boiling water bath for 24 hours a mixture of:
18.25 g of 2,5-dimethoxy-3-chloro-4-hydroxytetrahydrofuran
91 ml of 5.48 N ethylamine
10 ml of 10 N NaOH After 5 hours of heating there are added 45.5 ml of ethylamine as supplement.

After the conclusion of the heating period the solution is evaporated to dryness under reduced pressure. The residue is taken up in alcohol and the mineral salts are eliminated by filtration. Evaporation to dryness under reduced pressure is repeated and by distillation, 15.3 g of the compound indicated above are isolated.

Table 1 below summarizes Examples 1–18 illustrating the preparation and properties of the compounds of formula (III) (including the 4 compounds described above).

The different columns of the said Table 1 indicate the Example No., the values of $R_1$, $R_2$, $R_3$, Method of preparation (A or B) and procedure (a, b, c or d), duration of the heating in hours, yield in %, boiling point in °C/mm Hg., melting point, in °C; percentages of C, H and N by elementary analysis, percentage of N by protometry and calculated values for percentages of C, H and N.

Insofar as the melting and boiling points are concerned, it is to be noted that, as indicated above, the compounds of formulae (III) and (IV) present cis-trans isomerism at the level of the methoxy groups in positions 2 and 5. The substituents in positions 3 and 4 can also increase the number of possible isomers. In the course of preparation of these compounds, no attempt was made to separate the isomers and for this reason the boiling points are often spread over a range of temperatures that is somewhat broad. Further the melting points are not particularly significant because they were determined on mixtures of isomers whose proportion may vary from one procedure to the next.

It is to be noted that the melting points above 50°C were determined on a Koffler bench: melting points below 50°C were not determined.

The compound of Example 14 was imperfectly separated from the starting amine, the mixture containing 78% of the compound of Example 14 and 22% of the starting amine. These percentages were determined by measurement of the nitrogen. Preparation of compounds of formula (IV)

Example 19 — preparation of [(2,5-dimethoxy-4-hydroxy)tetrahydrofuryl-3-trimethyl ammonium] methosulfate having the formula:

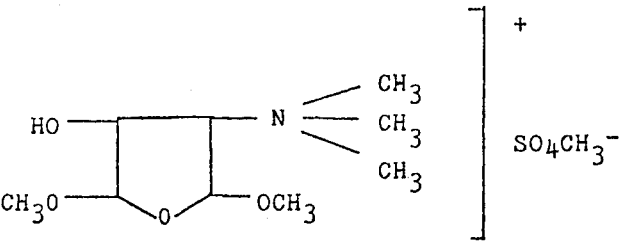

To 1.6 g of 2,5-dimethoxy-3-dimethylamino-4-hydroxytetrahydrofuran in 10 ml ether, there is added drop by drop with cooling, 0.88 ml of dimethyl sulfate. The quaternary ammonium salt separates very rapidly. The mixture is allowed to stand for 2 hours and then the solvent is decanted. The residue is washed twice with ether and dried under reduced pressure. 2.53 g of the above indicated quaternary ammonium salt are collected, representing a 96% yield.

Example 20 — Using an alternative procedure to a solution of 20.3 g of 2,5-dimethoxy 3-dimethylamino-4-hydroxytetrahydrofuran in 30 ml acetone, there is added, drop by drop, a solution of 12.6 g dimethyl sulfate in 30 ml acetone. The resulting solution is left standing at ambient temperature for 16 hours. Then the mixture is heated to boiling for 3 hours. An abundant precipitate is formed. The reaction mixture is then cooled to −20°C and filtered thereby providing a yield of 85%, i.e. 26.8 g of the above quaternary ammonium salt exhibiting a melting point of 122°C.

The result of analysis of this compound appears in Table 2.

Example 21 — preparation of [(2,5-dimethoxy-4-hydroxytetrahydrofuryl-3-dimethyl benzyl ammonium] chloride having the formula:

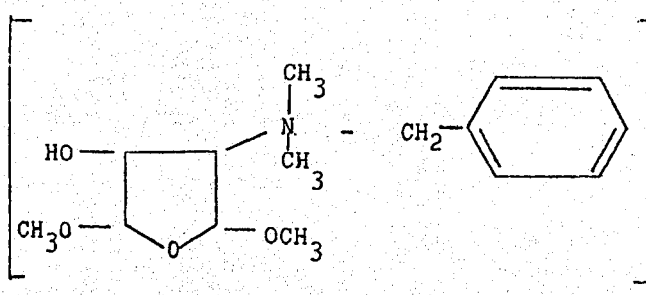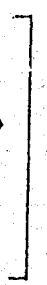

A solution of 20.2 g of (2,5-dimethoxy-3-dimethylamino-4-hydroxy) tetrahydrofuran in 40 ml acetone is mixed with a solution of 12.7 g benzyl chloride in 20 ml acetone. The resulting solution is left standing for 2 hours at ambient temperature, after which it is heated under reflux for 4 hours. The reaction mixture is then allowed to cool to room temperature and the precipitate that forms is filtered therefrom.

20.3 g of the quaternary ammonium salt of the above formula which represents a 64% yield is obtained, the salt exhibiting a melting point of 178°C.

The result of the analysis of this compound appears in Table 2.

Example 22 — preparation of [(2,5-dimethoxy-4-hydroxy) tetrahydrofuryl-3-methyl diethyl ammonium] paratoluene sulfonate, of the formula:

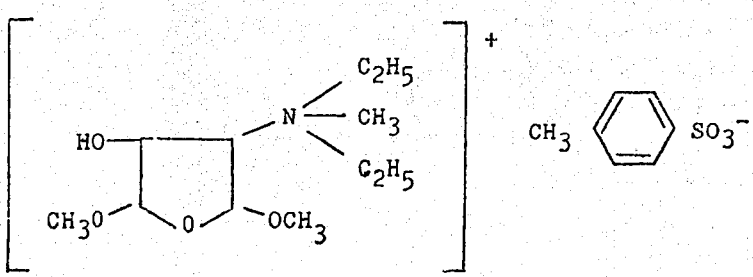

A solution of 13.0 g 2,5-dimethoxy-4-hydroxy-3-diethylaminotetrahydrofuran in 25 ml methylethylketone is mixed with a solution of 10.6 g of methyl paratoluene sulfonate in 25 ml methylethylketone. The solutions are left in contact for 16 hours. The precipitate that forms is filtered, and there is obtained 8.5 g of the sought compound. Melting point: 142°C.

The mother liquors are heated to boiling for 5 hours, then cooled to −20°C. The precipitate that forms is filtered and recrystallized in acetone. There is thus obtained 7.2 g of the compound, melting point = 138°C.

Total yield is 68%.

Results of the analysis appear in Table 2.

Example 23 — Preparation of [(2,5-dimethoxy-4-hydroxy) tetrahydrofuryl-3-methyl morpholinium] paratoluene sulfonate having the formula:

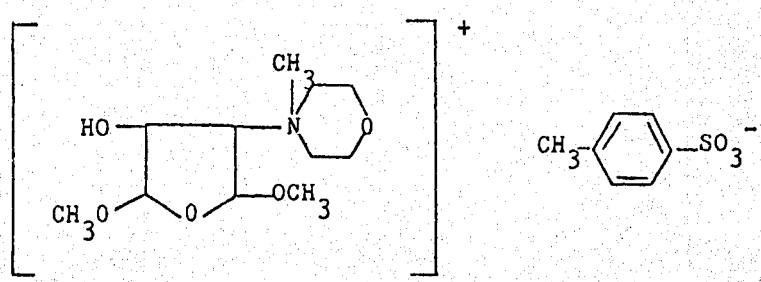

A solution of 23.9 g 2,5-dimethoxy-4-hydroxy-3-morpholino tetrahydrofuran in 50 ml methylethylketone is mixed with a solution of 18.6 g dimethyl paratoluene sulfonate in 30 ml methylethylketone. The resulting solution is heated at reflux for 9 hours. The solvent is then evaporated under reduced pressure and the residue is taken up in 350 ml water. This aqueous solution is then clarified with activated charcoal, commercially available as "Norit", and the water is evaporated under reduced pressure. The residue is crystallized in a 1:2 mixture of acetone and ethyl acetate. There are obtained 24.9 g of the above product exhibiting a melting point of 124°/128°C, which amount represents a 60% yield.

The result of the analysis appears in Table 2.

Example 24 — preparation of [(2,5-dimethoxy-4-hydroxy tetrahydrofuryl-3-methyl piperidinium] methane sulfonate having the formula:

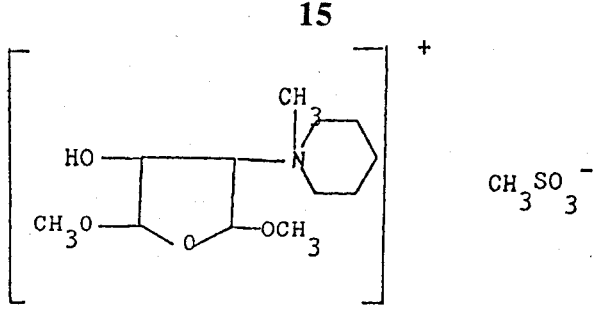

A solution of 23.3 g of (2,5-dimethoxy-4-hydroxy-3-piperidino) tetrahydrofuran in 50 ml methylethylketone is mixed with a solution of 11 g of methyl methane sulfonate in 30 ml methylethylketone. The resulting mixture is heated to reflux for 7 hours after which it is cooled to −20°C. 27.8 g of the above compound are obtained in crystalline form, melting at 120°–122°C, and representing a yield of 82%.

The result of the analysis appears in Table 2.

Table 2 below summarizes the characteristics of the quaternary ammonium salts of formula (IV) prepared above.

The different columns of Table 2 indicate the Example No., the values of $R_1$, $R_2$, $R_3$ and X, the melting point, in °C, the percentage found for the various constituents: C, H, N and Cl, by elementary analysis as well as the theoretical percentages (calculated values).

PREPARATION OF AMINATED ALDEHYDES HAVING FORMULAE (I) AND (II)

Aldehydes of formulae (I) and (II) are prepared by acid hydrolysis of corresponding compounds of formulae (III) and (IV). Some examples of hydrolysis are presented in the use examples which appear hereinafter.

Some of these aldehydes have been characterized by preparing their bis dinitrophenyl hydrazone hydrochloride.

Table 3 summarizes the characteristics of these compounds.

In this Table appear the meaning of $R_1$ and $R_2$, melting points with decomposition, percentage contents of C, H, N by elementary analysis as well as their theoretical percentages (calculated values) and finally the corresponding formula.

TABLE 1

| Example | $R_1$ | $R_2$ | $R_3$ | Method of Preparation | Heating Period (Hours) | Yield % |
|---|---|---|---|---|---|---|
| 3 | H | H | — | B(c) | 20 | 79 |
| 5 | H | —CH$_3$ | — | B(c) | 20 | 62 |
| 4 | H | —C$_2$H$_5$ | — | B(d) | 24 | 80 |
| 6 | H | —C$_3$H$_7$ | — | B(d) | 28 | 84 |
| 7 | H | —CH(CH$_3$)$_2$ | — | B(d) | 44 | 58 |
| 8 | H | —C$_4$H$_9$ | — | B(d) | 44 | 79 |
| 9 | H | —C$_6$H$_{13}$ | — | B(d) | 33 | 80 |
| 10 | H | —CH$_2$—CH$_2$—OH | — | A(b) | 24 | 80 |
| 11 | H | —C$_6$H$_{11}$ (cyclohexyl) | — | B(d) | 44 | 65 |

| Example No. | Boiling Point °C/mm Hg. | Melting Point °C | Analysis Found | | | N% By Protometry | Analysis Theoretical | | |
|---|---|---|---|---|---|---|---|---|---|
| | | | C% | H% | N% | | C% | H% | N% |
| 3 | 90–98/0.1 | 66 | 43.46 | 7.59 | 8.26 | 8.2 | 44.2 | 7.98 | 8.59 |
| | | | 43.70 | 7.61 | 8.34 | | | | |
| 5 | 87–91/0.3 | 58 | 47.09 | 7.88 | 8.07 | 7.84 | 47.4 | 8.46 | 7.91 |
| 4 | 98–100/0.5 | <50 | 49.70 | 8.61 | 7.47 | 7.14 | 50.3 | 8.91 | 7.34 |
| | | | 49.90 | 8.94 | 7.43 | | | | |
| 6 | 85–95/0.08 | 52 | 52.91 | 9.24 | 6.65 | 6.7 | 52.8 | 9.2 | 6.82 |
| | | | 52.22 | 8.70 | 6.80 | | | | |
| 7 | 99–102/0.9 | 62 | 51.88 | 8.82 | 6.29 | 6.67 | 52.8 | 9.2 | 6.82 |
| | | | 51.44 | 8.91 | 6.42 | | | | |
| 8 | 103–106/0.1 | 52 | 52.71 | 9.55 | 6.46 | 6.4 | 54.8 | 9.6 | 6.4 |
| | | | 53.86 | 9.29 | 6.23 | | | | |
| 9 | 118–126/0.1 | <50 | 58.15 | 10.06 | 5.19 | 5.54 | 58.3 | 10.1 | 5.66 |
| | | | 57.84 | 10.07 | 5.31 | | | | |
| 10 | 150–160/0.06 | | 46.30 | 8.29 | 6.4 | 6.75 | 46.37 | 8.27 | 6.76 |
| | | | 46.50 | 8.43 | 6.56 | | | | |
| 11 | 127–132/0.8 | 86 | 58.21 | 9.42 | 5.69 | 5.38 | 58.7 | 9.4 | 5.7 |
| | | | 58.33 | 9.35 | 5.72 | | | | |

| Example No. | $R_1$ | $R_2$ | $R_3$ | Method of Preparation | Heating Period (Hours) | Yield % |
|---|---|---|---|---|---|---|
| 12 | H | —C$_6$H$_5$ (phenyl) | — | B(d) | 34 | 29 |
| 13 | H | —CH$_2$—C$_6$H$_5$ | — | B(d) | 33 | 67 |
| 14 | H | —CH(CHO)—CHOH(CHO) | — | A(a) | 45 | 24 |

TABLE 1-continued

| Example | $R_1$ | $R_2$ | $R_3$ | Method of Preparation | Heating Period (Hours) | Yield % |
|---|---|---|---|---|---|---|
| 1 | H— | —$CH_2$—$CH_2$—NH—CH—CHOH<br>  $\|$   $\|$<br>  CHO  CHO | — | A(a) | 108 | 90 |
| 15 | $CH_3$ | $CH_3$ | — | B(c) | 22 | 75 |
| 16 | $C_2H_5$ | $C_2H_5$ | — | B(d) | 44 | 76 |
| 17 | $CH_2$—$CH_2$—OH | $CH_2$—$CH_2$—OH | — | A(b) | 24 | 85 |
| 2 | piperidinyl | | — | A(b) | 48 | 83 |
| 18 | morpholinyl | | — | A(b) | 72 | 76 |

| Example No. | Boiling Point °C/mm Hg. | Melting Point °C | Analysis Found | | | N% By Proto-metrg | Analysis Theoretical | | |
|---|---|---|---|---|---|---|---|---|---|
| | | | C% | H% | N% | | C% | H% | N% |
| 12 | 137–140/0.08 | <50 | 59.38<br>59.35 | 6.84<br>6.84 | 5.27<br>5.43 | 5.84 | 60.2 | 7.12 | 5.86 |
| 13 | 130–146/0.07 | <50 | 60.88<br>60.76 | 7.17<br>7.55 | 5.03<br>4.97 | 5.55 | 61.6 | 7.52 | 5.53 |
| 14 | 150–180/0.05 | — | | | | 5.43 | | | 4.53 |
| 1 | | | 46.98<br>46.58 | 7.94<br>7.82 | 7.8<br>8.0 | 7.88 | 47.75 | 7.95 | 7.95 |
| 15 | 86–100/0.1 | 50 | 49.44<br>49.74 | 8.19<br>8.30 | 7.36<br>7.47 | 6.94 | 50.2 | 8.9 | 7.3 |
| 16 | 85–98/0.06 | — | 54.77<br>54.62 | 9.52<br>9.47 | 5.77<br>6.03 | 6.03 | 54.7 | 9.7 | 6.4 |
| 17 | 180–195/0.07 | | 47.27<br>47.29 | 8.26<br>8.39 | 5.84<br>6.03 | 5.6 | 47.8 | 8.42 | 5.5 |
| 2 | 110–119/0.07 | | 57.12 | 9.34 | 6.03 | 6.05 | 57.12 | 9.15 | 6.06 |
| 18 | 108–122/0.03 | | 51.38<br>51.27 | 8.22<br>8.12 | 5.84<br>5.92 | 5.82 | 51.5 | 8.1 | 6.00 |

TABLE 2

| Example No. | $R_1$ | $R_2$ | $R_3$ | $X^-$ | Melting Point (°C) |
|---|---|---|---|---|---|
| 20 | $CH_3$ | $CH_3$ | $CH_3$ | $CH_3SO_4^-$ | 122 |
| 21 | $CH_3$ | $CH_3$ | $CH_2$– | $Cl^-$ | 178 |
| 22 | $C_2H_5$ | $C_2H_5$ | $CH_3$ | $CH_3$––$SO_3^-$ | 142 |
| 23 | morpholinyl | | $CH_3$ | $CH_3$––$SO_3^-$ | 124<br>128 |
| 24 | piperidinyl | | $CH_3$ | $CH_3SO_3^-$ | 120<br>122 |

| Example No. | Analysis Found | | | | Analysis Theoretical | | | |
|---|---|---|---|---|---|---|---|---|
| | C% | H% | N% | Cl% | C% | H% | N% | Cl% |
| 20 | 37.93<br>38.11 | 7.09<br>7.23 | 4.17<br>4.28 | — | 37.8 | 7.26 | 4.41 | |
| 21 | 56.56<br>56.81 | 7.30<br>7.55 | 4.17<br>4.45 | 10.95 | 56.6 | 7.55 | 4.41 | 11 |
| 22 | 53.22<br>53.38 | 7.63<br>7.79 | 3.36<br>3.39 | — | 53.31 | 7.70 | 3.45 | |
| 23 | 51.53<br>51.56 | 7.00<br>7.06 | 3.23 | | 51.53 | 6.96 | 3.34 | |
| 24 | 46.01<br>46.13 | 8.05<br>7.93 | 4.16 | | 45.59 | 8.24 | 4.09 | |

TABLE 3

Hydrochloride of Bix Dinitrophenylhydrazone of a few Aldehydes

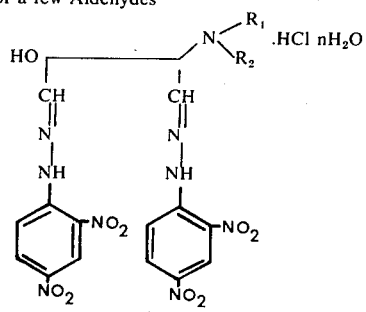

| $R_1$ | $R_2$ | Melting Point with decomposition, °C | Analysis Found C% | H% | N% | Analysis-Theoretical C% | H% | N% | for the formula |
|---|---|---|---|---|---|---|---|---|---|
| H | H | 180–188 | 34.78 | 3.02 | 22.46 | 34.95 | 3.66 | 22.92 | $C_{16}H_{15}O_9N_9.HCl.2H_2O$ |
| H | —$CH_3$ | 160–165 | 37.44 | 3.51 | 22.19 | 37.40 | 3.69 | 23.09 | $C_{17}H_{17}O_9N_9.HCl.H_2O$ |
| H | —$C_2H_5$ | 160–168 | 39.31 | 3.58 | 22.48 | 38.61 | 3.96 | 22.51 | $C_{18}H_{19}O_9N_9.HCl.H_2O$ |
| H | —$C_3H_7$ | 156–162 | 39.75 | 4.18 | 21.87 | 39.76 | 4.21 | 21.96 | $C_{19}H_{21}O_9N_9.HCl.H_2O$ |
| H | —CH(CH$_3$)$_2$ | 160–175 | 40.29 | 4.11 | 21.63 | 39.76 | 4.21 | 21.96 | $C_{19}H_{21}O_9N_9.HCl.H_2O$ |
| H | —$C_4H_9$ | 150–162 | 39.77 | 4.24 | 21.94 | 40.85 | 4.45 | 21.44 | $C_{20}H_{23}O_9N_9.HCl.H_2O$ |
| H | —$C_6H_{13}$ | 137–142 | 42.84 | 4.61 | 20.47 | 42.89 | 4.90 | 20.46 | $C_{22}H_{27}O_9N_9.HCl.H_2O$ |
| H | —C$_6$H$_{11}$ (cyclohexyl) | 164–172 | 42.81 | 4.30 | 20.48 | 43.03 | 4.59 | 20.53 | $C_{22}H_{25}O_9N_9.HCl.H_2O$ |
| H | —$CH_2$C$_6$H$_5$ | 155–165 | 44.10 | 3.56 | 20.42 | 44.41 | 3.88 | 20.27 | $C_{23}H_{21}O_9N_9.HCL.H_2O$ |

EXAMPLES OF USE

Example 34

The following tanning composition is prepared:

| | |
|---|---|
| 8% solution of 2-amino-3-hydroxy succinic aldehyde | 40 ml |
| Ethyl alcohol, 96° titer | 40 ml |
| White glycerol | 2 ml |
| Perfume | 1 g |
| Na$_2$CO$_3$, q.s.p. for pH = 2 | |
| Water, q.s.p. | 100 ml |

This composition is applied regularly to all parts of the body that one wishes to tan.

At the end of 2 or 3 minutes a light coloration appears which after 15 minutes assumes a very natural brown tone. This shade is rather resistant. However, if the shade is considered to be too dark, it can be lightened by washing with water and soap, makeup remover milk or eau de Cologne.

A product of this kind is much appreciated especially for "harmonizing" or "touching up" e.g. when there are white marks left by eyeglass frames on the nose or by shoulder straps on the shoulders.

Example 34 is repeated except that the 2-amino-3-hydroxy succinic aldehyde is replaced by an essentially equivalent amount of 2-ethylamino-3-hydroxy succinic aldehyde.

Example 35

The following composition in the form of white milk is prepared:

| | | |
|---|---|---|
| Cetyl stearyl alcohol, partly oxyethylenated (sold commercially as "Sipol wax" by the Sinnova Company - France) | 2.5 | g |
| Wheat starch | 2 | g |
| Mixture of methyl, ethyl, butyl and benzyl esters of para hydroxybenzoic acid (sold commercially as "Nipa ester 82521" by Nipa Company U.S.) | 0.19 | g |
| Phenyl polysiloxane (sold commercially as "Rhodorsil Oil 47 V. 300" by Rhone-Poulenc Company-France) | 0.2 | g |
| 10% solution of 2-methylamino 3-hydroxysuccinic aldehyde | 20 | g |
| Na$_2$CO$_3$, 2N, q.s.p. for pH 3 | | |
| Perfume | 0.5 | g |
| Water, q.s.p. | 100 | g |

When evenly applied to the skin, this milk affords a golden coloration in less than 10 minutes. The color reaches its maximum in at least an hour, looking just like natural tan. The coloration is resistant to baths, even in sea water.

Example 36

The following oleo-alcohol composition is prepared:

| | | |
|---|---|---|
| Colza oil | 2 | g |
| Isopropyl myristate | 25 | g |
| Ethyl alcohol, 96° titer | 60 | g |
| Perfume | 0.5 | g |
| 18% solution of 2-benzylamino-3-hydroxysuccinic aldehyde (the pH being adjusted to 3 by means of Na$_2$CO$_3$ | 12.5 | g |

This composition is introduced into an aerosol can and, after sealing, 70 g of dichlorodifluoromethane are added. This composition is sprayed on any part of the body that is to be tanned. At the end of 15 minutes a light coloration begins to appear, which then darkens to a bronzed hue. This color resists fresh water, sea water, washing with soap, and makeup removers.

Example 37

There is prepared a solution of 2-amino-3-hydroxy succinic aldehyde, by heating for 10 minutes in a boiling water bath, 519 mg of 2,5-dimethoxy-3-amino-4-hydroxy tetrahydrofuran in 10 cc N HCl. The pH of this solution is adjusted to between 3 and 4 by the addition thereto of sodium carbonate.

Bleached hair is impregnated with the above solution and heated under a hood for 30 to 45 minutes. At the end of this contact period, the hair is shampooed, rinsed and dried. The thus treated hair has an improved appearance, is flexible and more lively.

Example 38

A solution of 3-hydroxy-2-propylaminosuccinic aldehyde is prepared by heating for one hour in a boiling water bath 2.78 g of 2,5-dimethoxy 2-hydroxy-3-propylamino tetrahydrofuran in 33.5 cc 1N HCl. The pH of this solution is adjusted to between 3 and 4 by the addition thereto of sodium carbonate.

As indicated in Example 37, previously bleached hair is treated with the solution thus prepared. The results are just as good as those reported in Example 37.

Example 39

A solution of 2[[2-(1,2-diformyl-2-hydroxy)ethylamino]ethyl]amino-3-hydroxy succinic aldehyde (also called ethylene diamino N,N'-bis (3-hydroxysuccinic)aldehyde having the formula:

$$HO-CH-CH-N-CH-CHOH$$
$$\phantom{HO-}|\phantom{CH}|\phantom{CH-N}|\phantom{CH-}|$$
$$\phantom{HO-}CHO\phantom{~}CHO\phantom{~~~}CHO\phantom{~}CHO$$

is prepared by heating for one hour over a boiling water bath, 608 mg of 3,3' ethylene diamino bis(4-hydroxy-2,5-dimethoxy) tetrahydrofuran in 10 ml 1N HCl. The pH of this solution is adjusted to 3.5 by the addition thereto of sodium carbonate.

As indicated in Example 37, previously bleached hair is treated with the solution thus prepared. The results are just as good as those achieved in Examples 37 and 38.

Example 40

A solution of 3-hydroxy-2-piperidino succinic aldehyde is prepared by heating for 5 hours over a boiling water bath 3.5 of g 2,5-dimethoxy 3-hydroxy-4-piperidino tetrahydrofuran in 40 cc of 1N HCl. The pH of this solution is adjusted to 4 by the addition thereto of sodium carbonate.

As indicated in Example 37, previously bleached hair is treated with the solution thus prepared and the results obtained are just as good as those reported in Examples 37–39.

Example 41

A solution of quaternary ammonium salt of 3-hydroxy-2-trimethylammonium succinic aldehyde is prepared by dissolving 2.53 g of 2,5-dimethoxy-4-hydroxy-3-trimethylammonium tetrahydrofuran methosulfate in 15 ml 1N NaOH and adding to this solution after it has stood overnight, at ambient temperature, 15 ml of 2N HCl and heating for 43 hours over a boiling water bath. The pH of this solution is adjusted between 3 and 4 by the addition thereto of sodium carbonate.

As indicated in Example 37, previously bleached hair is treated with the solution thus prepared. The results obtained are just as good as in the previous examples.

Example 42

The following composition is prepared:

| | | |
|---|---|---|
| 0.376 M solution of 2-isopropyl-amino-3-hydroxy succinic aldehyde | 50 | cc |
| Ethyl alcohol, 96° titer | 40 | cc |
| Glycerine | 2 | cc |
| Perfume | 0.1 | cc |
| Sodium bicarbonate, q.s.p. | pH 3 | |
| Water, q.s.p. | 100 | cc |

The resulting composition when applied to those parts of the body desired to be tanned, imparts thereto a brown shade.

Example 42 is repeated except that the 2-isopropylamino-3-hydroxy succinic aldehyde is replaced by (a) 2-propyl-3-hydroxy succinic aldehyde, (b) 2-di-β-hydroxyethylamino-3-hydroxy succinic aldehyde, (c) 2-[(1,2-diformyl-2-hydroxy) ethylamino]-3-hydroxy succinic aldehyde (d) 2[[2-(1,2-diformyl-2-hydroxy) ethylamino]ethyl] amino-3-hydroxy succinic aldehyde and (e) 2-dimethylamino-3-hydroxysuccinic aldehyde. Good results were achieved in all five cases.

Example 43

The following composition is prepared:

| | | |
|---|---|---|
| 0.372 M Solution of 2-butylamino-3-hydroxy succinic aldehyde | 15 | cc |
| Oleyl alcohol condensed with 10 moles ethylene oxide | 5 | g |
| Carboxymethyl cellulose | 2 | g |
| Orthohydroxy quinoline sulfate | 0.1 | g |
| Silicone oil | 1 | g |
| 2N sodium carbonate, q.s.p. | pH 3 | |
| Perfume | 1 | g |
| Water, q.s.p. | 100 | g |

This composition is applied to the skin to be tanned. The desired, very natural brown color appears ten minutes following application. The resistance of the coloration achieved to even soapy water increases with the length of the application time.

Example 44

Tanning Milk

| | | |
|---|---|---|
| Cetyl stearyl alcohol condensed with 13 moles ethylene oxide | 7 | g |
| Phenyl polysiloxane (sold under the name "Rhodorsil Oil 47 V 300" by Rhone-Poulenc Company) | 1 | g |
| Diethyleneglycol stearate | 6 | g |
| Methyl parahydroxy benzoate | 0.1 | g |
| Propyl parahydroxy benzoate | 0.1 | g |
| 0.411 M solution of 2-hexylamino-3-hydroxy succinic aldehyde | 25 | cc |
| 2N sodium carbonate, q.s.p. | pH 2.5 | |
| Water, q.s.p. | 100 | g |

When applied to the skin, this bronzing or tanning milk reaches maximum intensity of coloration in about two hours. The coloration is a very natural golden shade which resists removal by water.

Example 45

Tanning Cream

| | | |
|---|---|---|
| Cetyl stearyl alcohol condensed with 13 moles of ethylene oxide | 2.6 | g |
| Cetyl alcohol | 2.6 | g |
| Stearic acid | 0.6 | g |
| Castor oil | 6.85 | g |
| Sweet almond oil | 1.3 | g |
| $C_{12}$-$C_{14}$ alcohol condensed with 10.5 moles ethylene oxide | 0.3 | g |
| Ethyl para amino benzoate | 0.2 | g |
| Isopropyl myristate | 4.5 | g |
| Perfume | 0.3 | g |
| 0.372 M solution of 2-cyclohexyl-amino-3-hydroxy succinic aldehyde | 35 | cc |
| 2 N sodium carbonate, q.s.p. | pH 3.5 | |
| Water, q.s.p. | 100 | cc |

The resulting cream is colored light beige and when applied on the portions of the skin to be tanned, the coloration starts to appear in about 15 minutes and reaches its maximum intensity in about 2 hours. The color obtained is a pretty natural chestnut shade which resists quite well even soapy water. Example 46

10 grams of previously bleached hair are impregnated with 25 cc of a solution of 0.425 M 2-hydroxy-3-trimethylammonio succinic aldehyde prepared by acid hydrolysis of the corresponding tetrahydrofuran. The pH of the solution is adjusted to 3 by the addition thereto of sodium bicarbonate. The solution is permitted to remain in contact with the hair for 30 minutes at a temperature of 50°C, after which the hair is rinsed and dried. As a result of this treatment the hair has an improved appearance, is more flexible and more soft.

Example 47

To hair which has previously been permanently waved there is applied a 0.512 M solution of 2-hydroxy-3-dimethyl benzyl ammonio succinic aldehyde prepared by acid hydrolysis of the corresponding tetrahydrofuran. The pH of said solution being adjusted to 4 by the addition thereto of sodium bicarbonate. This solution is permitted to remain in contact with the hair for 40 minutes at 30°C, after which the hair is rinsed and dried. The thus treated hair has a very agreeable look and is more soft to the touch than the hair prior to said treatment. Example 48

Bleached hair is impregnated for a period of 30 minutes at 30°C with a 0.362 M solution of 2-hydroxy-3-diethylmethyl ammonio succinic aldehyde prepared by acid hydrolysis of the corresponding tetrahydrofuran. The pH of the solution is adjusted to 3.5 by the addition thereto of sodium bicarbonate. The thus treated hair is then rinsed after which a hair setting lotion comprising 0.4% aqueous solution of a copolymer of polyvinyl pyrrolidone and vinyl acetate having a viscosity of 3.5 to 4 centipoises in a 5% solution in ethanol having a pH of 3.5 is applied thereto. The hair is then rolled on curlers and dried. Excellent results are obtained including the imparting of a brilliant sheen to the hair.

Example 49

Previously bleached hair is impregnated with a 0.437 M solution of 2-hydroxy-3-(methyl morpholino) succinic anhydride, the pH of which had been adjusted to 2.5 by the addition thereto of powdered sodium carbonate. The solution remained in contact with the hair for a period of 30 minutes at a temperature of 45°C. The hair was then rinsed and set in the customary way.

After drying the hair is more easy to style and less electric than hair not treated with said solution.

Example 50

To previously bleached hair there is applied for a period of about 30 minutes at 50°C the following solution:

| | | |
|---|---|---|
| 0.484 M solution of 2-hydroxy-3-(methyl piperidino) succinic aldehyde | 100 | cc |
| Sodium bicarbonate, q.s.p. | pH 3 | |

Thereafter the hair is rinsed, rolled on curlers and dried under a hood. The hair thus treated is lively and less electric and more easy to style than hair not treated as described.

Example 51

To hair that has been previously bleached and then dyed, there is applied a 0.353 M solution of 2-diethylamino-3-hydroxy succinic aldehyde, the pH of which has been adjusted to 2.5 by the addition thereto of sodium carbonate. The solution is permitted to remain in contact with the hair for a period of 30 minutes at 50°C. The hair is then rinsed, set in the usual fashion and dried under a hood. The thus treated hair is more brilliant and less subject to tangling than hair not treated with the solution described above.

Example 52

Previously bleached hair is shampooed with an acidic cationic shampoo composition and then dried. Thereafter the hair is impregnated with 100 cc of a 0.268 M solution of 2-bis-($\beta$-hydroxyethyl amino-3-hydroxy succinic aldehyde, the pH of which has been adjusted to 2.5 by the addition thereto of sodium bicarbonate, for a period of about 30 minutes at 45°C. To the thus treated hair there is then applied the following hair setting solution:

| | | |
|---|---|---|
| Copolymer of polyvinylpyrrolidone and vinyl acetate 60/40 having a viscosity of 3.5 to 4 centipoises in 5% solution in ethanol | 5 | g |
| Ethyl alcohol, 96° titer | 25 | cc |
| Trimethyl cetyl ammonium bromide | 0.1 | g |
| Powdered sodium bicarbonate, q.s.p. | pH 2.5 | |
| Water, q.s.p. | 100 | cc |

The hair is then rolled on curlers and again saturated with the above hair setting solution. After drying, the hair is lively and holds a good set.

Example 53

An oleo-ethanolic composition for tanning the skin is prepared as follows:

| | | |
|---|---|---|
| Olive oil | 4 | g |
| Isopropyl palmitate | 35 | g |
| Ethyl alcohol - 96° titer | 48 | g |
| Perfume | 0.5 | g |
| 16% solution of 2-butylamino-3-hydroxy succinic aldehyde (pH being adjusted to 4.75 by triethanol amine) | 12.5 | g |

This composition is packaged in an aerosol container and after sealing, there are introduced 70 g of dichlorodifluoromethane.

The composition when sprayed onto those portions of the body desired to be tanned, immediately produces a medium brown coloration which resists fading by water.

Example 54

An oleo-ethanolic composition for tanning the skin is prepared as follows:

| | | |
|---|---|---|
| Cocoa oil | 0.5 | g |
| Isopropyl myristate | 10 | g |
| Ethyl alcohol, 96° titer | 75 | g |
| Perfume | 0.5 | g |
| 12% solution of 2-ethylamino-3-hydroxy succinic aldehyde (pH being adjusted to 3.5 by triethanol amine) | 14 | g |

This composition is packaged in an aerosol container and after sealing, 70 g of dichlorodifluoromethane are introduced therein.

The composition when sprayed onto those portions of the body to be tanned immediately produces a medium brown color which is resistant to fading by water.

Example 55

An oleo-ethanolic composition for tanning the skin is prepared as follows:

| | | |
|---|---|---|
| Peanut oil | 2 | g |
| Isopropyl palmitate | 20 | g |
| Ethyl alcohol, 96° titer | 63 | g |
| Perfume | 0.5 | g |
| 15% solution of 2-benzylamino-3-hydroxy succinic aldehyde (pH being adjusted to 3 by triethanolamine) | 12.5 | g |

This composition is packaged in an aerosol container and after sealing, there are introduced 70 g of dichlorodifluoromethane.

The composition when sprayed onto those portions of the body to be tanned produces in about 15 minutes a light coloration which then darkens to a bronzed hue over the succeeding 5 hour period. The color achieved is resistant to fading by water.

Example 56

An oleo-ethanolic composition for tanning the skin is prepared as follows:

| | | |
|---|---|---|
| Peanut oil | 5 | g |
| Isopropyl myristate | 40 | g |
| Ethyl alcohol, 96° titer | 44.5 | g |
| Perfume | 0.5 | g |
| 18% solution of 2-di-$\beta$-hydroxy-ethylamino-3-hydroxy succinic addehyde (pH being adjusted to 3.8 with triethanolamine) | 10 | g |

This composition is packaged in an aerosol container and after sealing the same 70 g of dichlorodifluoromethane are introduced therein.

The composition when sprayed onto those parts of the body to be tanned immediately produces a golden brown coloration.

Example 57

An oleo-ethanolic composition for tanning the skin is prepared as follows:

| | | |
|---|---|---|
| Palm oil | 0.2 | g |
| Isopropyl palmitate | 5 | g |
| Ethyl alcohol, 96° titer | 74.3 | g |
| Perfume | 0.5 | g |
| 14% solution of 2-hexylamino-3-hydroxy succinic aldehyde (the pH being adjusted to 3 with triethanolamine) | 20 | g |

This composition is packaged in an aerosol container, and after sealing, 70 g of dichlorodifluoromethane are introduced therein.

The composition when sprayed onto those parts of the body to be tanned imparts thereto after about 20 minutes, a golden shade which is resistant to fading by water.

Example 58

An aqueous gel formation for tanning the skin is prepared as follows:

| | | |
|---|---|---|
| 9% solution of 2-propylamino-3-hydroxy succinic aldehyde | 20 | cc |
| Nonylphenol oxyethylenated with 8 moles of ethylene oxide | 10 | g |
| Ethyl cellulose | 1 | g |
| Methyl para-hydroxy benzoate | 0.1 | g |
| Silicone oil | 1 | g |
| Sodium carbonate, 2N, q.s.p. | pH | 5 |
| Perfume | 1 | g |
| Water, q.s.p. | 100 | g |

This composition when applied to those parts of the body to be tanned immediately imparts thereto a brownish coloration.

Example 59

An aqueous gel composition for tanning the skin is prepared as follows:

| | | |
|---|---|---|
| 18.8% solution of 2-($\beta$-hydroxy-ethylamino)-3-hydroxy succinic aldehyde | 25 | cc |
| Oleyl alcohol condensed with 12 moles of ethylene oxide | 9 | g |
| Methyl cellulose | 2.5 | g |
| Ortho-hydroxy quinoline sulfate | 0.1 | g |
| Sodium carbonate, 2N, q.s.p. | pH 3 | |
| Perfume | 1 | g |
| Water, q.s.p. | 100 | g |

This composition when applied to those parts of the body to be tanned, instantly provides an intense golden brown coloration.

Example 60

An aqueous gel composition for tanning the skin is prepared as follows:

| | | |
|---|---|---|
| A solution of 0.855 mole of 2-[(1,2-diformyl-2-hydroxy)ethylamino]-3-hydroxy succinic aldehyde of the formula HO—CH—CH—NH—CH—CHOH $\quad\quad$ \|$\quad$\|$\quad\quad\quad$\|$\quad$\| $\quad\quad$ CHO CHO $\quad$ CHO CHO | 10 | cc |
| Lauryl alcohol oxyethylenated with 6 moles of ethylene oxide | 13 | g |
| Isopropyl cellulose | 1.5 | g |
| Ortho-hydroxy quinoline sulfate | 0.1 | g |
| Silicone oil | 0.8 | g |
| Sodium carbonate, 2N, q.s.p. | pH 3 | |
| Perfume | 1 | g |
| Water, q.s.p. | 100 | g |

This composition when applied to those parts of the body to be tanned provide yellow brown coloration 10 minutes after application.

Example 61

An aqueous gel composition for tanning the skin is prepared as follows:

Carboxylic derivative of imidazole of the formula $$C_{11}H_{23}-C\underset{\underset{N}{\|}}{\overset{OH}{\overset{|}{-}}}N\underset{\underset{CH_2}{\diagdown\diagup}}{\overset{\diagup CH_2-COONa}{\diagdown CH_2-CH_2-CH_2-O-CH_2-COONa}}$$

| | | |
|---|---|---|
| sold under the name "MIRANOL C2M" | 3 | g |
| Crosslinked polyacrylic acid sold under the mark "CARBOPOL 934" | 1.5 | g |
| 11% solution of 2-benzylamino-3-hydroxy succinic aldehyde | 36 | g |
| Water, q.s.p. | 100 | g |
| | pH = 4.5 | |

This gel when applied uniformly on the skin produces after a 15 minute period a light brown coloration which intensifies and stabilizes at the end of 5–8 hours to a bronzed hue. The coloration achieved remarkably resists fading by soft water and sea water.

Example 62

An aqueous gel composition for tanning skin is prepared as follows:

| | | |
|---|---|---|
| Carboxylic derivative of imidazole (as in Example 61) | 3 | g |
| Cross-linked polyacrylic acid sold under the name "CARBOPOL 940" | 0.8 | g |
| 6% solution of 2-methylamino-3-hydroxy succinic aldehyde | 12 | g |
| Sodium carbonate, 2N, q.s.p. | pH 5.5 | |
| Water, q.s.p. | 100 | g |

This gel when applied uniformly on the skin provides in less than 10 minutes an intense brown coloration.

Example 63

An oil-in-water emulsion composition for tanning the skin is prepared as follows:

| | | |
|---|---|---|
| Cetyl-stearyl alcohol (30%–70%) partially oxyethylenated and sold under the name "Cire de Sipol AO" (F°=46°C; iodine number ≤ 2; hydroxy number = 185–190) | 5 | g |
| Light vaseline oil | 6 | g |
| Isopropyl myristate | 3 | g |
| White glycerine | 10 | g |
| Perfume | 0.3 | g |
| 17% solution of 2[[2-(1,2-diformyl-2-hydroxy)ethylamino]ethyl] amino-3 hydroxy succinic aldehyde (also called ethylene diamino N,N'-bis (3-hydroxy succinic aldehyde) of the formula: | 20 | g |
| HO—CH—CH—NH—CH₂—CH₂—NH—CH—CHO<br>       │    │                           │   │<br>       CHO CHO                       CHO CHO | | |
| Sodium carbonate, 2N, q.s.p. | pH 4 | |
| Water, q.s.p. | 100 g | |

$$HO-\underset{\underset{CHO}{|}}{CH}-\underset{\underset{CHO}{|}}{CH}-NH-CH_2-CH_2-NH-\underset{\underset{CHO}{|}}{CH}-CHO$$

This cream when applied to those portions of the body to be tanned provides, in less than 10 minutes, a chestnut coloration which resists fading by water.

Example 64

An oil-in-water emulsion composition for tanning the skin is prepared as follows:

| | | |
|---|---|---|
| Cetyl-stearyl alcohol (30%–70%) partially oxyethylenated and sold under the name "Cire de Sipol AO" | 6 | g |
| Perhydrosqualene | 4 | g |
| Isopropyl myristate | 2 | g |
| White glycerine | 15 | g |
| Perfume | 0.3 | g |
| 19% solution of 2-isopropylamino-3-hydroxy succinic aldehyde | 30 | g |
| Sodium carbonate, 2N, q.s.p. | pH 4 | |
| Water, q.s.p. | 100 | g |

This composition when applied to the body provides very rapidly a medium brown coloration.

Example 65

An oil-in-water emulsion composition for tanning the skin is prepared as follows:

| | | |
|---|---|---|
| Cetyl-stearyl alcohol (30%–70%) partially oxyethylenated and sold under the name "Cire de Sipol AO" | 3 | g |
| Light vaseline oil | 7 | g |
| Isopropyl palmitate | 10 | g |
| Light glycerine | 8 | g |
| Crosslinked polyacrylic acid sold under the name "CARBOPOL 941" | 5 | g |
| Perfume | 0.3 | g |
| 12% solution of 2-ethylamino-3-hydroxy succinic aldehyde | 20 | g |
| Sodium carbonate, 2N, q.s.p. | pH 4.75 | |
| Water, q.s.p. | 100 | g |

This cream when applied to the skin provides very rapidly a medium brown coloration.

Example 66

An oil-in-water emulsion composition for tanning the skin is prepared as follows:

| | | |
|---|---|---|
| Vaseline oil | 18 | g |
| Glycerine | 4.5 | g |
| Stearyl alcohol oxyethylenated and sold under the name "POLAWAX CP 200" | 2.4 | g |
| 15% solution of 2-hexylamino-3-hydroxy succinic aldehyde | 29 | g |
| Sodium carbonate, 2N, q.s.p. | pH 3.5 | |
| Water, q.s.p. | 60 | g |

This composition is packaged in an aerosol container and after sealing, 10 g of dichlorodifluoromethane are added. When the composition is applied as a foam on these portions of the body to be tanned, a golden shade is produced in 15 minutes and is intensified and stabilized after about 5–8 hours. The coloration achieved resists fading by water remarkably well.

Example 67

An oil-in-water emulsion composition for tanning the skin is prepared as follows:

| | | |
|---|---|---|
| Cetyl-stearyl alcohol (10% sulfated - 90% not sulfated) sold under the name "Cire de Lanette SX" | 3 | g |
| Isopropyl myristate | 5 | g |
| Olive oil | 0.5 | g |
| Lauryl alcohol oxyethylenated with 12 moles of ethylene oxide | 0.5 | g |
| Palm oil | 0.2 | g |
| Perfume | 0.5 | g |
| Cetyl alcohol | 4 | g |
| Crosslinked polyacrylic acid sold under the name "CARBOPOL 940" | 0.5 | g |
| 8% solution of 2-dimethylamino-3-hydroxy succinic aldehyde | 5 | g |
| Triethanolamine, q.s.p. | pH 5.2 | |
| Water, q.s.p. | 100 | g |

This cream when applied to the skin instantly imparts thereto an intense brown coloration.

What is claimed is:

1. A cosmetic composition for coloring the skin having a pH between 2–5 and consisting essentially of a solution containing 1. 0.5–12 percent by weight of an aminated aldehyde of the formula

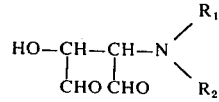

wherein $R_1$ is selected from the group consisting of hydrogen, methyl and hydroxyethyl, $R_2$ is selected from the group consisting of hydrogen, methyl, ethyl, propyl, isopropyl, butyl, hexyl, hydroxyethyl, cyclohexyl, benzyl, (1,2-diformyl-2-hydroxy) ethyl and 2-[(1,2-diformyl-2-hydroxy) ethylamino] ethyl and $R_1$ and $R_2$ together with the nitrogen atom to which they are attached form piperidinyl;

2. 0.2–5 percent of a member selected from the group consisting of colza oil, olive oil, peanut oil, cocoa oil and palm oil;

3. 5–40 percent by weight of a lower alkyl ester selected from the group consisting of isopropyl myristate and isopropyl palmitate; and 4. 35–80 percent by weight of ethanol.

2. The composition of claim 1 wherein said aldehyde is selected from the group consisting of 2-amino-3-hydroxysuccinic aldehyde, 2-methylamino-3-hydroxysuccinic aldehyde, 2-ethylamino-3-hydroxy- succinic aldehyde, 2-butylamino3-hydroxysuccinic aldehyde, 2-propylamino-3-hydroxysuccinic aldehyde, 2-isopropylamino-3-hydroxysuccinic aldehyde, 2-di-β-hydroxyethylamino-3-hydroxysuccinic aldehyde, 2-hexylamino-3-hydroxysuccinic aldehyde, 2-benzylamino-3-hydroxysuccinic aldehyde, 2-cyclohexylamino-3-hydroxysuccinic aldehyde, 2-[(1,2-diformyl-2-hydroxy)ethylamino]-3-hydroxysuccinic aldehyde 2[[2-(1,2-diformyl-2-hydroxy)ethylamino]ethyl]amino-3-hydroxysuccinic aldehyde and 2-dimethylamino-3-hydroxysuccinic aldehyde.

3. A cosmetic composition for coloring the skin having a pH between 2–5 and consisting essentially of
1. 1–15 weight percent of a surface active agent selected from the group consisting of (A) fatty alcohol having 12-18 carbon atoms and oxyethylenated with 4–15 moles of ethylene oxide, (B) nonylphenol oxyethylenated with 6–12 moles of ethylene oxide and (C)

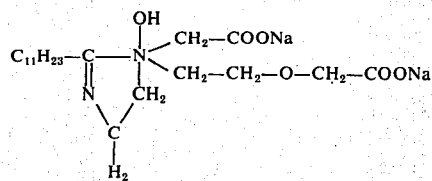

2. 0.5–4 weight percent of a thickening agent selected from the group consisting of
A. cellulose ether,
B. carboxymethyl cellulose and
C. crosslinked polyacrylic acid having a Brookfield viscosity, measured in a 0.5% solution neutralized to a pH of 7 with NaOH, of 8,900 – 43,000 centipoises;

3. 0–2 weight percent of silicone oil;
4. 0.5–12 weight percent of an aminated aldehyde of the formula

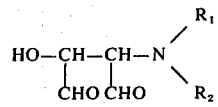

wherein $R_1$ is selected from the group consisting of hydrogen, methyl and hydroxyethyl, $R_2$ is selected from the group consisting of hydrogen, methyl, ethyl, propyl, isopropyl, butyl, hexyl, hydroxyethyl, cyclohexyl, benzyl, (1,2-diformyl-2-hydroxy) ethyl and 2-[(1,2-diformyl-2-hydroxy) ethylamino] ethyl and $R_1$ and $R_2$ together with the nitrogen atom to which they are attached form piperidinyl; and 5. the remainder consisting essentially of water.

4. The composition of claim 3 wherein said aldehyde is selected from the group consisting of 2-amino-3-hydroxysuccinic aldehyde, 2-methylamino-3-hydroxysuscinic aldehyde, 2-ethylamino-3-hydroxy-3-succinic aldehyde, 2-butylamino-3-hydroxysuccinic aldehyde, 2-propylamino-3-hydroxysuccinic aldehyde, 2-isopropylamino-3-hydroxysuccinic aldehyde, 2-di-β-hydroxyethylamino-3-hydroxysuccinic aldehyde, 2-hexylamino-3-hydroxysuccinic aldehyde, 2-benzylamino-3-hydroxysuccinic aldehyde, 2-cyclohexylamino-3-hydroxysuccinic aldehyde, 2-[(1,2-diformyl-2-hydroxy)ethylamino]-3-hydroxysuccinic aldehyde, 2[[2-(1,2-diformyl-2-hydroxy) ethylamino]ethyl]amino-3-hydroxysuccinic aldehyde and 2-dimethylamino-3-hydroxysuccinic aldehyde.

5. A cosmetic composition for coloring the skin having a pH between 2–5 and consisting essentially of
1. 2–15 percent by weight of a fatty alcohol having 12–18 carbon atoms oxyethylenated with 10–15 moles of ethylene oxide as a surface active agent;
2. 0–20 percent by weight of a component selected from the group consisting of light vaseline oil, perhydrosqualene, sweet almond oil, ricin oil, colza oil, olive oil, peanut oil, cocoa oil, palm oil, isopropyl palmitate, isopropyl myristate, fatty alcohol having 16 carbon atoms and saturated fatty acid having 18 carbon atoms;
3. 0–6 percent by weight of a thickening agent selected from the group consisting of (A) starch, (B) crosslinked polyacrylic acid having a Brookfield viscosity measured in a 0.5% solution neutralized to a pH of 7 with NaOH of 8,900 – 43,000 centipoises, (C) diethylene glycol stearate;
4. 0–15 weight percent glycerine; and
5. 0.5–12 weight percent of an aminated aldehyde of the formula

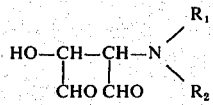

wherein $R_1$ is selected from the group consisting of hydrogen, methyl and hydroxyethyl, $R_2$ is selected from the group consisting of hydrogen, methyl, ethyl, propyl, isopropyl, butyl, hexyl, hydroxyethyl, cyclohexyl, benzyl, (1,2-diformyl-2-hydroxy) ethyl and 2-[(1,2-diformyl-2-hydroxy) ethylamino] ethyl and $R_1$ and $R_2$ together with the nitrogen atom to which they are attached form piperidinyl; and 6. the remainder consisting essentially of water.

6. The composition of claim 5 wherein said aldehyde is selected from the group consisting of 2-amino-3-hydroxysuccinic aldehyde, 2-methylamino-3-hydroxysuccinic aldehyde,
2-ethylamino-3-hydroxy-3-succinic aldehye, 2-butylamino-3-hydroxysuccinic aldehyde, 2-propylamino-3-hydroxysuccinic aldehyde, 2-isopropylamino-3-hydroxysuccinic aldehyde, 2-di-β-hydroxyethylamino-3-hydroxysuccinic aldehyde, 2-hexylamino-3-hydroxysuccinic aldehyde, 2-benzylamino-3-hydroxysuccinic aldehyde, 2-cyclohexylamino-3-hydroxysuccinic aldehyde, 2-[(1,2-diformyl-2-hydroxy)ethylamino]-3-hydroxysuccinic aldehyde, 2[[2-(1,2-diformyl-2-hydroxy)ethylamino]ethyl] amino-3-hydroxysuccinic aldehyde and 2-dimethylamino-3-hydroxysuccinic aldehyde.

7. A cosmetic composition for coloring the skin having a pH between 2–5 and consisting essentially of a solution in a solvent selected from the group consisting of water and an aqueous alcohol solution wherein the alcohol component is selected from the group consisting of ethanol and isopropanol present in an amount of about 10–90 weight percent of the total composition, of 0.5–12 percent by weight of said composition of an aminated aldehyde selected from the group consisting of 2-ethylamino-3-hydroxy succinic aldehyde, 2-propylamino-3-hydroxy succinic aldehyde, 2-di-β-hydroxyethylamino-3-hydroxy succinic aldehyde, 2-[(1,2-diformyl-2-hydroxy) ethylamino]-3-hydroxy succinic aldehyde, 2[[2-(1,2-diformyl-2-hydroxy) ethylamino]ethyl] amino-3-hydroxy succinic aldehyde and 2-dimethylamino-3-hydroxy succinic aldehyde.

8. The composition of claim 7 which also includes about 0.5–5 weight percent glycerine.

* * * * *

UNITED STATES PATENT OFFICE
CERTIFICATE OF CORRECTION

Patent No. 3,940,477          Dated May 8, 1974

Inventor(s)  Guy Vanlerberghe et al.

It is certified that error appears in the above-identified patent and that said Letters Patent are hereby corrected as shown below:

The term of this patent subsequent to

May 21, 1991, has been disclaimed.

Signed and Sealed this twenty-ninth Day of June 1976

[SEAL]

Attest:

RUTH C. MASON
*Attesting Officer*

C. MARSHALL DANN
*Commissioner of Patents and Trademarks*